United States Patent [19]

Marquardt

[11] Patent Number: 4,849,221

[45] Date of Patent: Jul. 18, 1989

[54] PHARMACEUTICAL PRODUCT, CONTAINING A MIXTURE OF BENZOIC ACID, PHENOL AND AN ALKALI FLUORIDE, FOR THE TOPICAL TREATMENT OF HERPES VIRUS EFFLORESCENCES, AND METHOD FOR TREATMENT OF HERPES SIMPLEX EFFLORESCENCES IN THE HUMAN

[76] Inventor: Bernd Marquardt, Auf der Heide 1c, D-4040 Neuss, Fed. Rep. of Germany

[21] Appl. No.: 110,701

[22] PCT Filed: Dec. 11, 1986

[86] PCT No.: PCT/EP86/00737

§ 371 Date: Oct. 13, 1987

§ 102(e) Date: Oct. 13, 1987

[87] PCT Pub. No.: WO87/03482

PCT Pub. Date: Jun. 18, 1987

[30] Foreign Application Priority Data

Dec. 12, 1985 [DE] Fed. Rep. of Germany ....... 3543801

[51] Int. Cl.$^4$ .............................................. A01N 59/10
[52] U.S. Cl. ................................................... 424/676
[58] Field of Search ............................................ 424/151

[56] References Cited

U.S. PATENT DOCUMENTS

| 3,337,412 | 8/1967 | Elbreder | 424/151 |
| 4,363,794 | 12/1982 | Ochiai et al. | 424/151 |
| 4,568,540 | 2/1986 | Asano et al. | 424/151 |
| 4,624,851 | 11/1986 | Revici | 424/151 |

FOREIGN PATENT DOCUMENTS

3543801 6/1987 Fed. Rep. of Germany.

OTHER PUBLICATIONS

Rote Liste 1985 (with translation).

*Primary Examiner*—A. Lionel Clingman
*Assistant Examiner*—Willie J. Thompson
*Attorney, Agent, or Firm*—Dennis P. Clarke

[57] ABSTRACT

The present invention relates to pharmaceutical products containing a mixture of benzoic acid, phenol and an alkali fluoride, in an aqueous or aqueous-alcohol solution, optionally in the presence of other usual additives for pharmaceutical preparations, in liquid or semi-liquid form, for the control of diseases in the human caused by herpes virus, and to methods for the topical treatment with these products of herpes simplex efflorescences in the human.

5 Claims, No Drawings

PHARMACEUTICAL PRODUCT, CONTAINING A MIXTURE OF BENZOIC ACID, PHENOL AND AN ALKALI FLUORIDE, FOR THE TOPICAL TREATMENT OF HERPES VIRUS EFFLORESCENCES, AND METHOD FOR TREATMENT OF HERPES SIMPLEX EFFLORESCENCES IN THE HUMAN

The present invention relates to a novel pharmaceutical product containing a mixture of benzoic acid, phenol and an alkali fluoride in an aqueous or aqueous-alcohol solution, optionally in the presence of other usual additives for pharmaceutical preparations in liquid or semi-liquid form, and its use for controlling herpes-virus-caused diseases in the human.

Herpes-virus-caused diseases in the human generally induce a more or less pronounced formation of blisters, and especially on human mucous membranes they cause the formation of sometimes very painful or extremely itchy blisters. A particularly well known form of such diseases is herpes simplex.

A product that contains both benzoic acid and phenol and sodium fluoride is on the market and is used highly diluted with water as a disinfectant for the area of the mouth. Unexpectedly, mixtures of benzoic acid, phenol and an alkali fluoride, preferably sodium fluoride, in an aqueous or aqueous-alcohol solution, which optionally contains other usual additives for pharmaceutical preparations in liquid or semi-liquid form, in a form not highly diluted with water, are suitable for rapid and effective control of herpes-virus-caused diseases in the human, in particular for external treatment of the diseased areas of the skin, especially mucous membrane areas.

The individual components are known in numerous pharmaceutical preparations. For instance, benzoic acid and phenol are used as antiseptics, and sodium fluoride is used for caries prevention.

The pharmaceutical product according to the invention for controlling herpes-virus-caused diseases in the human is characterized in that for 100 g of end product, it contains, besides water or water-alcohol as a solvent and besides typical additives for pharmaceutical preparations in liquid or semi-liquid form, from 0.1 to 0.5 g of the alkali fluoride, in particular sodium fluoride, preferably from 0.2 to 0.4 g of benzoic acid, from 0.6–0.8 g of phenol, and from 0.2 to 0.4 g of the alkali fluoride.

EXAMPLE 1

100 g of an aqueous solution contain 0.65 g of a 1:5 solution of benzoic acid in ethyl alcohol, 0.73 g of phenol and 0.22 g of sodium fluoride. The product additionally contains 5.88 g of menthol oil, 1.2 g of 01 carbophylli, 1.63 g of methyl salicylate and 0.74 g of p-ethyl hydroxybenzoate.

The ingredients are intimately mixed and poured into containers having a stopper of a kind such that the stopper can be used to apply the product drop by drop to the affected areas.

EXAMPLE 2

100 g of an aqueous solution contain 2.4 g of a 1:5 solution of benzoic acid in ethyl alcohol (0.4 g of benzoic acid and 2.0 g of 96% alcohol), 1 g of phenol and 0.4 g of sodium fluoride. It contains no additives, for improving the odor, for example. The ingredients are processed as in example 1.

I claim:

1. A pharmaceutical product containing a mixture of benzoic acid, phenol and an alkali fluoride, in an aqueous or aqueous-alcohol solution, optionally in the presence of other usual additives for pharmaceutical preparations, in liquid or semi-liquid form, for the topical treatment of herpes virus efflorescenes.

2. A pharmaceutical product as defined by claim 1, characterized in that the alkali fluoride is sodium fluoride.

3. A pharamaceutcal product as defined by claim 1, characterized in that 100 g of the product contain from 0.1 to 0.5 g of benzoic acid, from 0.5 to 1.0 g of phenol and from 0.1 to 0.5 g of the alkali fluoride.

4. A phameceutical product as defined by claim 3, characterized in that 100 g of the product contains from 0.2 to 0.4 g of benzoic acid, 0.6 to 0.8 g of phenol and 0.2 to 0.4 g of the alkali fluoride.

5. A method for the topical treatment of herpes simplex efflourescences, characterized in that a product defined by claim 1 is applied to the efflorescence once or or a plurality of times.

* * * * *

UNITED STATES PATENT AND TRADEMARK OFFICE
CERTIFICATE OF CORRECTION

PATENT NO. : 4,849,221

DATED : July 18, 1989

INVENTOR(S) : BERND MARQUARDT

It is certified that error appears in the above-identified patent and that said Letters Patent is hereby corrected as shown below:

Claim 1, column 2, line 30, delete "efflorescenes" and insert therefor --efflorescences--;

Signed and Sealed this

Twelfth Day of June, 1990

Attest:

HARRY F. MANBECK, JR.

*Attesting Officer*      *Commissioner of Patents and Trademarks*